US007666636B2

(12) United States Patent
Yezza et al.

(10) Patent No.: US 7,666,636 B2
(45) Date of Patent: Feb. 23, 2010

(54) PROCESS FOR PRODUCING POLY-β-HYDROXYBUTYRATE

(75) Inventors: Abdessalem Yezza, Montreal (CA); Jalal Hawari, Saint Laurent (CA)

(73) Assignee: National Research Council of Canada, Ottawa, Ontario (CA)

( * ) Notice: Subject to any disclaimer, the term of this patent is extended or adjusted under 35 U.S.C. 154(b) by 345 days.

(21) Appl. No.: 11/715,944

(22) Filed: Mar. 9, 2007

(65) Prior Publication Data

US 2007/0249027 A1    Oct. 25, 2007

Related U.S. Application Data

(60) Provisional application No. 60/784,482, filed on Mar. 22, 2006.

(51) Int. Cl.
*C12P 7/62* (2006.01)
*C12N 1/20* (2006.01)
(52) U.S. Cl. .................... 435/135; 435/252.3
(58) Field of Classification Search ............ None
See application file for complete search history.

(56) References Cited

U.S. PATENT DOCUMENTS 5,268,422 A * 12/1993 Yalpani .............. 525/54.2
5,502,273 A    3/1996 Bright et al.
6,083,729 A    7/2000 Martin et al.

FOREIGN PATENT DOCUMENTS

CA    2460109    3/2004

OTHER PUBLICATIONS

Agriculture and Agri-Food Canada, 2005. Canadian Maple Products: Situation and Trends (2004-2005). www.agr.gc.ca/misb/hort/sit/pdf/maplerable0506_e.pdf.
Barham PG, Keller A, Otum EL, Holmes A. 1984. Crystallization and morphology of a bacterial thermoplastic: poly-β-hydroxybutyrate. J Mater Sci 19:2781-2794.
Braunegg G, Bona R, Koller M. 2004. Sustainable polymer production. Polymer-Plastics Technology and Engineering 43:1779-1793.
Byrom D, 1990. Industrial production of Copolymer from *Alcaligenes eutrophus*. In: Dawes EA, ed. Novel Biodegradable Microbial Polymers. Amsterdam: Kluwer Academic. p. 113-117.
Comeau Y, et al. 1988. Determination of poly-β-hydroxybutyrate and poly-hydroxyvalerate in activated sludge by gas-liquid chromatography. Appl Environ Microbiol 54:2325-2327.
Cox MK. 1994. Properties and applications of polyhydroxyalkanoates. In: Doi Y and Fukuda K editors. Biodegradable plastics and polymers. Amsterdam: Elsevier Science p. 120-135.
Doi Y. 1990. Microbial polyesters. New York: VHC Publishers Inc. 156 p.
Frazzetto G, 2003. White biotechnology. EMBO Reports 4:835-837.
Gavrilescu M, Chisti Y. 2005. Biotechnology: a sustainable alternative for chemical industry. Biotechnol Adv 23:471-499.

Gerngross TU. 1999. Can biotechnology move us toward a sustainable society? Nature Biotechnology 17:541-544.
Gerngross TU, Slater SC. 2000. How green are green plastics? Scientific American 283:37-41.
Gross RA, Kalra B. 2002. Biodegradable Polymers for the Environment. Science 297:803-807.
Grothe E, et al. 1999. Fermentation optimization for the production of poly (β-hydroxybutyric acid) microbial thermoplastic. Enzyme Microbial Technol 25:132-141.
Huyler NK. 2000. Cost of maple sap production for various size tubing operations. U.S. Dept. of Agriculture, Forest Service, Newtown Square, PA.
Lee SN, Lee MY, Park WH. 2002. Thermal stabilization of poly(3-hydroxybutyrate) by poly(glycidyl methacrylate). J Appl Polymer Sci 83:2945-2952.
Morin A, et al. 1995. Exopolysaccharide production on low-grade maple sap by *Enterobacter agglomerans* grown in small scale bioreactors. J Appl Bacteriol 79:30-37.
Morselli MF, et al. 1996. Maple chemistry and quality. In: North American maple syrup producers manual. Columbus: The Ohio State University. p. 162-171.
Palleroni NJ, Palleroni AV. 1978. *Alcaligenes latus*, a new species of hydrogen-utilizing bacteria. Int J Sys Bacteriol 28:416-424.
Pradella JG. 2006. Biopolimeros e Intermediarios Quimicos. Relatorio Tecnico # 84396-205, Sao Paulo, Brazil, p. 80.
Rehm BHA, 2003. Polyester synthases: Natural catalysts for plastics. Biochem J 376:15-33.
Steinbuchel A, et al. 1992. Molecular basis for biosynthesis and accumulation of polyhydroxyalkanoic acids in bacteria. FEMS Microbiol Rev 103:217-230.
Wang F, et al. Poly(3-hydroxybutyrate) production with high productivity and high polymer content . . . Appl Environ Microbiol 63:3703-3706, Sep. 1997.
Whitney GG, et al. 2004. Sweet trees, sour circumstances: The long search for sustainability . . . Forest Ecology and Management 200:313-333.
Woodward J, Orr M. 1998. Enzymatic conversion of sucrose to hydrogen. Biotechnol Progr 14:897-902.
Yamane T, et al. 1996. Increased PHB productivity . . . Biotechnol Bioeng 50:197-202.
Yezza A, et al. 2006. Production of Polyhydroxyalkanoates from Methanol . . . Appl Microbiol Biotechnol 73:211-218.
Lageveen RG, et al. 1988. Formation of polyesters by *Pseudomonas oleovorans*: . . . Appl. Environ. Microbiol. 54: 2924-2932.

(Continued)

*Primary Examiner*—Herbert J. Lilling
(74) *Attorney, Agent, or Firm*—Hans Koenig

(57) ABSTRACT

A process for producing poly-β-hydroxybutyrate (PHB) involves contacting maple sap with bacteria (e.g *Alcaligenes latus*) that convert sugars into poly-β-hydroxybutyrate. The use of maple sap is comparable to or better than the use of pure sucrose, and the use of maple sap results in PHB having higher weight average molecular weight than PHB produced from pure sucrose, making maple sap-derived PHB more suitable for commercial utilization.

11 Claims, 3 Drawing Sheets

OTHER PUBLICATIONS

Lee SY. 1996. Bacterial Polyhydroxyalkanoates. Biotechnol. Bioeng. 49: 1-14.

Lee SY. 1996. Plastic bacteria? Progress and prospects for polyhydroxyalkanoate production in bacteria. Trends Biotechnol. 14:431-438.

Lee SY, Choi J, Wong HH. 1999. Recent advances in polyhydroxyalkalonoate production by bacterial fermentation: minireview. Int. J. Biol. Macromol. 25:31-36.

Lee SY, et al. 2000. Production of medium-chain-length polyhydroxyalkanoates . . . Biotechnol. Bioeng. 86:466-470.

Morin A, et al. 1993. Effect of carbon, nitrogen, and agitation on exopolysaccharide production . . . Enzyme Microb. Technol. 15:500-507.

Quillaguamán J, et al. 2005. Poly(b-hydroxybutyrate) production by a moderate halophile, . . . J. App. Microbiol. 99:151-157.

Quillaguamán J, et al. 2007. Optimizing conditions for poly (b-hydroxybutyrate) production . . . Appl. Microbiol. Biotechnol. 74:981-986.

Reddy CSK, Ghai R, Kalia V. 2003 Polyhydroxyalkanoates: an overview. Bioresour. Tecnol. 87:137-146.

Steinbüchel A, Füchtenbush B. 1988. Bacterial and other biological system for polyester production. Trends Biotechnol. 16:419-427.

Wu Q, Huang H, Hu G, Chen J, Ho KP, Chen GQ. 2001. Production of poly-3-hydroxybutyrate by *Bacillus* sp. JMa5 cultivated in molasses media. Antonie van Leeuwenhoek 80:111-118.

\* cited by examiner

US 7,666,636 B2

PROCESS FOR PRODUCING POLY-β-HYDROXYBUTYRATE

CROSS-REFERENCE TO RELATED APPLICATIONS

This application claims the benefit of U.S. Provisional application U.S. Ser. No. 60/784,482 filed Mar. 22, 2006.

FIELD OF THE INVENTION

The present invention relates to a process for producing poly-β-hydroxybutyrate, particularly to bioconversion of maple sap into poly-β-hydroxybutyrate.

BACKGROUND OF THE INVENTION

The current source for many chemicals and materials is petroleum. Nearly $24 billion (US) worth of hydrocarbon feedstock is used annually in the chemical industry (Gavrilescu and Chisti, 2005). Anticipation of its limited future availability, along with record high prices has spurred interest in alternatives that will be both sustainable and cost-effective. Hopeful visionaries have already started to talk about a "carbohydrate economy" replacing the old "hydrocarbon economy". It has been stated that carbohydrates are the "sleeping giant" of biotechnology and that carbohydrates will be the next century's feedstock alternative to petroleum-based products (Frazzetto, 2003). Using carbohydrate feedstock offers the possibility of creating biodegradable and thus environmentally friendly products, as well as providing a sustainable resource for the feedstock.

Maple sap is a naturally occurring, unprocessed crystal clear liquid, having the constituency and clarity of water, which derives from sugar-maple trees. It is a sweet and pure solution containing between 1 and 3% sugars mostly sucrose, traces of glucose and fructose, nitrogenous and phenolic compounds, organic acids as well as different minerals (Morselli and Whalen, 1996). Maple sap is one of the abundant and renewable sources of sugars, available in relatively large quantities in eastern Canada, particularly in Quebec ((Whitney and Upmeyer, 2004). The transformation of maple sap has traditionally been geared towards the production of maple syrup, the most important non-timber forest product in Canada. Over the last five years, Canada has accounted for 84% of the world's production of maple syrup, with the province of Quebec accounting for 92.9% of domestic production. However, the long-term economic survival of this industry in Quebec is being threatened by the year-over-year accumulation of inventory surpluses due to an imbalance between supply and demand of maple syrup products. According to the Quebec maple syrup producer's federation, the volume of bulk inventories accumulated in Quebec since 1999, before the 2005 harvest, was 60 million pounds (Agriculture and Agri-Food Canada, 2005). These figures suggest the immediate need to manage maple syrup surpluses and one alternative is developing new value added industrial applications by different biotechnological processes.

Apart from maple syrup and its co-products, little work has apparently been dedicated to the use of maple sap as a renewable feedstock for the chemical and material industries. Woodward and Orr (1998) showed that maple sap has the potential to be converted into hydrogen using enzymes, and Morin et al. (1995) used low grade maple sap as a raw material for exopolysaccharide production by *Enterobacter agglomeran*.

Recently, biodegradable plastics such as polyhydroxyalkanolates (PHAs), for example poly-β-hydroxybutyrate (PHB), have received increased attention because of their thermoplastic or elastomeric properties resembling those of petroleum-based plastics, yet are completely biodegradable (Steinbuchel et al., 1992). It is known that *Alcaligenes* and other bacteria can produce polyhydroxyalkanolates from pure sugar feedstocks. In addition to being produced biologically, these alternative polymeric materials are capable of being converted to relatively harmless degradation products, $CO_2$ and $H_2O$, through natural microbiological mineralization (Braunegg et al., 2004). To date such biotechnologically produced commercial polyesters have been from refined raw materials such as sugar cane and molasses in Brazil, sugar beets in Europe and corn in the United States. Such processes suffer from a number of disadvantages, including the need to refine the raw materials.

There is a need in the art for a more cost-effective process for the production of poly-β-hydroxybutyrate from unrefined raw materials.

SUMMARY OF THE INVENTION

Bioconversion of maple sap into valuable bioproducts is in its infancy. It has now been found that maple sap may be advantageously used as a feedstock for the production of poly-β-hydroxybutyrate (PHB) by bacteria. Thus, the present invention demonstrates that maple sap may be used as a carbon source for the production of poly-β-hydroxybutyrate (PHB) by bacteria.

In an aspect of the invention, there is provided a process for producing poly-β-hydroxybutyrate comprising contacting maple sap with bacteria that convert sugars into poly-β-hydroxybutyrate.

The poly-β-hydroxybutyrate produced in the process advantageously has a weight average molecular weight (Mw) of 435,000 Daltons or greater, preferably 450,000 Daltons or greater, more preferably 475,000 Daltons or greater, even more preferably 480,000 Daltons or greater.

The bacteria may comprise any bacteria or mixture of bacteria that can convert sugars, especially sucrose, to PHB. Such bacteria may include, for example, species of *Alcaligenes* (e.g. *A. latus, A. eutropha*), *Azotobacter* (e.g. *A. vinelandii*), *Escherichia* (e.g. recombinant *E. coli*), *Klebsiella* (e.g. *K. aerogenes, K. oxytoca*), *Nocardia, Pseudomonas, Rhizobium* and *Bacillus*. Species of *Alcaligenes* are particularly preferred, for example, *Alcaligenes latus* and *Alcaligenes eutrophus*. *Alcaligenes latus* is particularly preferred.

The use of maple sap, as opposed to other sources of sugars, is advantageous for one or more reasons. For example, PHB production results obtained from maple sap are reproducible and are comparable to or better than those obtained from pure sucrose. Use of maple sap results in PHB having higher weight average molecular than PHB produced from pure sucrose, making maple sap-derived PHB more suitable for commercial utilization. Higher yields of PHB are obtainable with maple sap as opposed to pure sucrose.

Further, maple sap can be harvested and then used in the process without further refining, thereby reducing production costs. The production cost of PHB from renewable resource is determined by the expenses related to raw materials and auxiliaries, utilities, capital stock, labour and other expenditures. Recent research indicates that PHB was uncompetitive when produced from corn-based processes in the United States, but it was found to be somewhat more competitive when produced from sugar mill-based processes in Brazil (Gross and Kalra, 2002). The cost of sugar production from sugarcane in Brazil is between $150-$200/ton, while the cost of glucose production from corn starch in the United States is about $450/ton. As a consequence, the production cost for PHB in Brazil is estimated to be about one third of that in the United States (Pradella, 2006). Moreover, the production of PHB using corn as a feedstock with current fermentation technology is thus of questionable environmental benefit, even under rather favorable assumptions Gerngross, 1999. Comparatively, according to a technical study produced by the United States Department of Agriculture (Huyler, 2000), the average annual operating cost per tap ranged from $4.64 for a 500 taps sugar bush operation to $1.84 for a sugar bush with 10,000 taps. During the season, an average tap will produce 6 to 10 gallons of sap at 2-3% sugar content. PHB produced from maple sap can have a significant cost advantage when compared to PHB produced in United States and Brazil, since maple sap does not need any refining steps, e.g. extraction and purification.

Production of PHB using maple sap as renewable feedstock can be adversely affected by factors mainly related to feedstock availability, consistency, seasonality and storability, which are common problems that face biomass technology. Maple sap collection, delivery and storage are elements of major importance in the plant economics. The storage of maple sap is an important issue for a bioconversion process that operates year-round, because of the seasonal harvesting of maple sap. To mitigate such problems, maple sap may be concentrated, for example by reverse osmosis which can remove 75% of the water from the sap, and stored at 4° C. To store maple sap, appropriate precautions should be taken to inhibit bacterial growth. On a commercial scale, PHB productivity may be increased by high-cell-density fed-batch culture, which provides an opportunity to greatly reduce the cost of PHB production.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
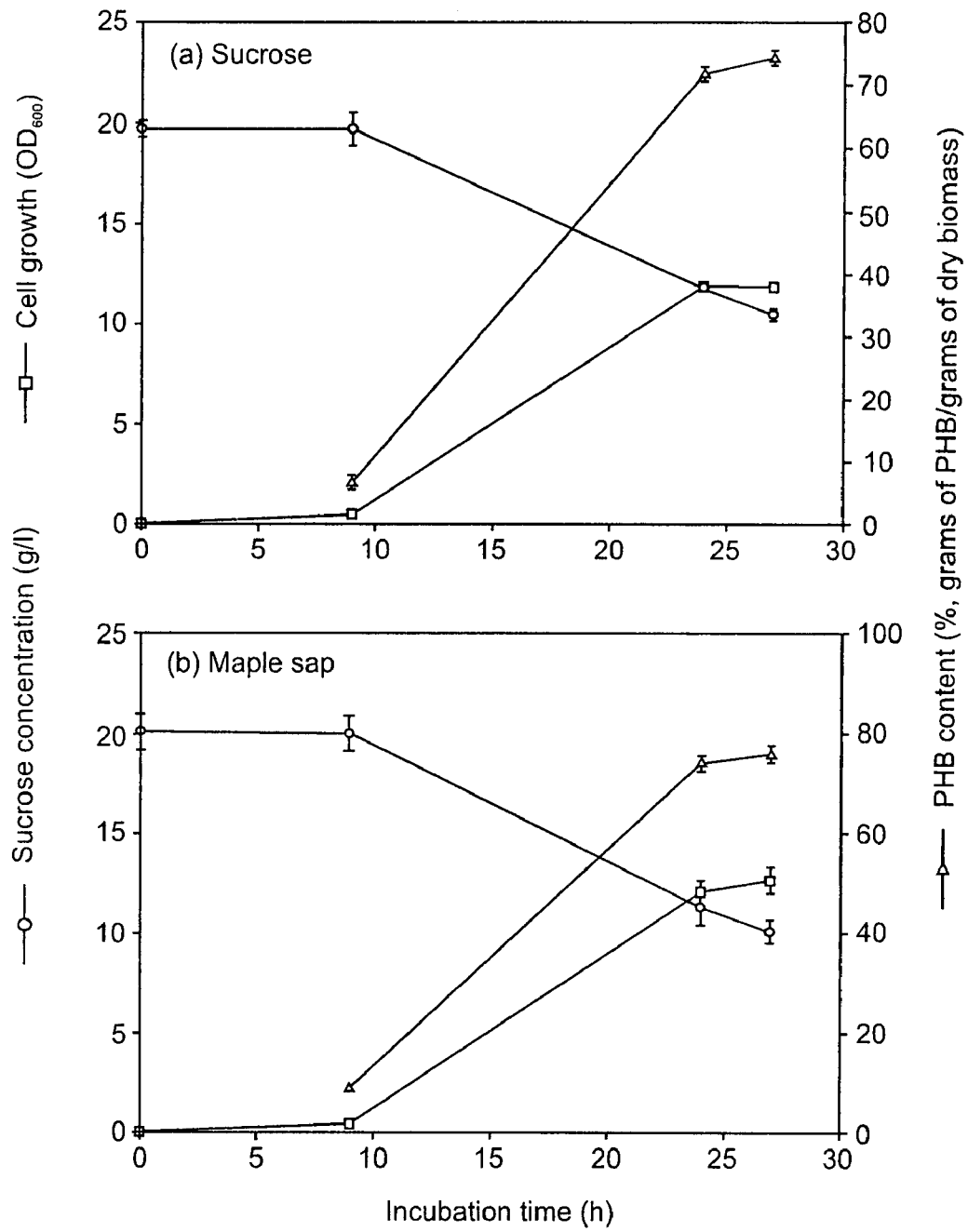
FIG. 1 depicts graphs of cell growth ($OD_{600}$), sucrose concentration (g/l) and PHB content (%, grams of PHB/grams of dry biomass) versus incubation time (h) for shake flask experiments of *Alcaligenes latus* grown in (a) sucrose and (b) maple sap.

Materials and Methods:

Pre-culture preparation: *Alcaligenes latus* (ATCC 29714) was acquired from the ATCC collection. The inoculum was prepared in two steps. Several colonies of *A. latus* were used to inoculate a 50 ml falcon tube containing 5 ml of sterilized nutrient broth medium (BD 234000, Difco) containing 5 g/l of meat peptone and 3 g/l of meat extract. After 24 h incubation at 33° C.±1° C. with an agitation rate of 200 rpm, the total volume was used to inoculate a 500 ml baffled shake flask containing 100 ml of sterile cultivation medium.

Cultivation media: *A. latus* was cultivated in a commercial sucrose-based medium and in maple sap media. The commercial sucrose-based medium having 20 g/l sucrose was modified medium 3 as described by Grothe et al. (1999), the disclosure of which is herein incorporated by reference. Maple sap media were prepared from maple sap samples collected from Érablière Les Frères Beaulieu Inc. (Ormstown, Quebec) and Érablière Pilon-Potvin (Bolton-Est, Quebec). Compositions of the maple samples are shown in Table 1. Maple sap samples were supplemented with 1 g/l $(NH_4)_2SO_4$ (a nitrogen source), 1.4 g/l $KH_2PO_4$, 1.8 g/l $Na_2HPO_4$, 1 g/l $MgSO_4$, and 1 ml/l trace elements to form the maple sap media. All cultivation media were adjusted to pH 7, passed through Steritcup™ filter unit (0.22 μm, Millipore Inc.) and used as feedstock for PHB production.

TABLE 1

Composition of Maple Sap Samples

| | Concentration | |
|---|---|---|
| | Beaulieu | Pilon-Potvin |
| Sucrose | 20 g/l | 31 g/l |
| Glucose | 0.8 g/l | 1.2 g/l |
| Fructose | 0.3 g/l | 0.5 g/l |
| Sodium | 0.7 mg/l | 8.7 mg/l |
| Potassium | 68 mg/l | 69 mg/l |
| Chloride | 15.5 mg/l | 14 mg/l |
| Phosphate | 1.8 mg/l | 5 mg/l |
| Sulphate | 31.3 mg/l | 55.8 mg/l |
| pH | 6.5-7 | 6.5-7 |
| Colour | Light yellow | Transparent/clear |

Fermentation Procedure:

Shake flask studies: A 5% (v/v) inoculum of the pre-culture was used to inoculate a 500 ml Erlenmeyer flask containing 100 ml sterilized maple sap or sucrose-based media. The flasks were then incubated at 33° C.±1° C. in an orbital shaking incubator (150 rpm) for 27 h.

Fermenter studies: Fermentations were carried out in stirred-tank bioreactor (20 L, Chemap AG, Männedorf, Switzerland, 10 L working volume) equipped with accessories and automatic control systems for DO, pH, antifoam, impeller speed, aeration rate and temperature. The computer program used allowed automatic set-point control and registration of all stated parameters.

Cultivation medium was added to the fermenter and sterilized in situ at 121° C. for 20 min. The medium was subsequently cooled to 33° C. and then inoculated (5% v/v) with a pre-culture of *Alcaligenes latus*. Aeration and agitation rates were variable to maintain the dissolved oxygen (DO) values above 30% of relative saturation. Foaming during fermentation was controlled using both mechanical foam breaker and a chemical antifoam agent (Biospumex™ 0.1 g/l aqueous emulsion).

Cell growth was monitored by measuring the absorbance of the fermentation broth at 600 nm ($A_{600}$). Samples were collected periodically and centrifuged (3000×g) for 10 minutes. The supernatant was analysed for sugars and ammonium nitrogen content. The biomass was washed twice with distilled water to remove residual culture media, frozen and then lyophilized for subsequent extraction and analysis of PHB.

Analytical Procedures:

Sugars and ammonia analysis: Residual carbon source concentration was measured using an HPLC from Waters (pump model 600 and auto-sampler model 717 plus; Waters Chromatography Division, Milford, Mass., USA) equipped with an ion-exchange column (Interaction ION-300, 300 mm by 7.8 mm; Interaction Chemicals Inc., CA, USA). The ammonium cation concentration was determined using an SP 8100 HPLC system equipped with a Waters 431 conductivity detector and a Hamilton PRP-X200 (250 mm×4.1 mm by 10 µm) analytical cation-exchange column.

Biopolymer quantification: Homopolymer (PHB) content produced by *A. latus* was determined as described by Comeau et al. (1988). Briefly, dry biomass was treated with acidified methanol in the presence of benzoic acid as an internal standard at 100° C. for 3 h to convert fatty acids released from the polymer to their corresponding methyl esters. The methyl esters were extracted in chloroform for subsequent analysis by a GC (Agilent 6890 GC-FID; Agilent Technologies Inc., Wilmington, USA) equipped with a capillary column SPB-1 (15 m×530 µm×0.15 µm; Agilent J&W GC Columns) connected to an FID detector. The injector and detector temperatures were set at 265° C. and 275° C., respectively. The oven temperature was set at 50° C. for 5 min and then increased at a rate of 30° C./min to 270° C. PHB content (%, w/w dry biomass) were expressed as percentage of polymer weight to lyophilized biomass weight. Poly[(R)-3-hydroxybutyric acid] (Fluka, Buchs, Switzerland) was used as reference standard, which was subjected to the same derivatization procedure described previously.

Biopolymer extraction and purification: Lyophilised cells were extracted for 12 h in chloroform to destroy the cell membranes and solubilize the polymer. Purification of biopolymers was done by methanol precipitation followed by centrifugation of the precipitated polymers and subsequently drying at room temperature.

Molecular weight determination: The weight average molecular weight (Mw) was determined by gel permeation chromatography (GPC), using a pump (Waters 510, Quebec, Canada), an auto-sampler (Waters 715 Ultra WISP, Quebec, Canada), a differential refractometer detector at 30° C. (Waters 410, Quebec, Canada) and a 60 cm PLgel 5 µL Mixed-C column with a linear range of molecular weight of 200-2,000,000 Daltons (Da) at room temperature. The mobile phase was chloroform ($CHCl_3$) with a flow rate of 1 ml/min. The dried PHB granules were dissolved in $CHCl_3$ and filtered through 0.45 µm polytetrafluoroethylene (PTFE) filter. A 0.06 ml volume of polymer solution was injected for each sample. Data collection and analysis were done with Waters Millennium software.

Thermal analysis characterization: The melting temperature (Tm) and crystallinity of purified PHB were measured using a Perkin Elmer Diamond differential scanning calorimeter (DSC). DSC is an excellent method for the thermal analysis of polymers, and can be used to measure the heat capacity of a sample as a function of temperature. Purified PHB samples (3-10 mg) were encapsulated in aluminum pans for measurements. Each sample was first brought and maintained at −20° C., then a temperature scan of 10° C./min from −20° C. to 220° C. was made. The sample was maintained at this temperature for 5 minutes and then a cooling scan at the same rate was performed from 220° C. to −20° C. A second run was recorded under the same conditions (isotherm, scanning rate and temperature range). First scan provides information on the sample's thermal history and the second, thermal information under the thermal program. Melting temperature (Tm) and enthalpy of fusion (ΔH) values were determined from the second scanned DSC thermograms. Crystallinity of PHB was estimated from the enthalpy of fusion (ΔH) obtained by DSC. The enthalpy of fusion of a theoretical 100% crystalline sample was assumed to be 146 J/g (Barham et al., 1984).

Thermogravimetric analysis (TGA) of PHB sample was performed using a TA Instruments TGA 2950. The analysis was carried out under nitrogen purge flow rate of 60 ml/min with a temperature scanning rate of 50° C./min.

Results:

Batch cultures of *Alcaligenes latus* were investigated and optimized for the production of the microbial thermoplastic PHB using maple sap as sole carbon source. Preliminary cultivation experiments were performed in baffled shake flasks to evaluate the use of maple sap as raw material for the production of PHB. FIG. 1 summarizes shake flask kinetics of *A. latus* on sucrose and maple sap. Regardless of the cultivation media, the cells had similar growth profiles, each starting with a lag phase of approximately 9 h. PHB content in both media increased proportionally with cell mass and the consumption of 9 to 10 g/l of sucrose.

Maple sap was successfully used as sole carbon sources to produce PHB by *A. latus*. After 27 h incubation in shake flasks, sucrose or maple sap base media produced, respectively, 2.9 g/l and 4.4 g/l cell dry weight biomass with a respective PHB content of 74.1 wt % and 77.6 wt % (percentage of PHB weight to cell dry weight) (see Table 2). Overall PHB yield was greater with maple sap, with 0.34 g/g (g PHB per g sugar) compared to 0.23 g/g in sucrose based media (see Table 2). The relative higher biomass and PHB content obtained with maple sap compared to pure sucrose based media may be attributed to the presence of other carbon sources such as glucose, fructose and organic acids in the sap which could be used by *A. latus* as supplementary growth substrate. *A. latus*, a wild-type PHA producing bacteria exhibits a remarkable capability of utilizing at least 67 different organic compounds, including sugars, acids, alcohol, aromatic compounds and amino acids, as carbon and energy sources for growth and for PHA accumulation (Palleroni and Palleroni, 1978). *A. latus* is particularly useful for industrial production as it has rapid growth in sucrose-rich media, polymer accumulation can be as high as 90% of the cell dry weight, polymer yields can be high, and it is harmless to the environment, animals and humans and is easily lysed for recovery.

Figure 2:
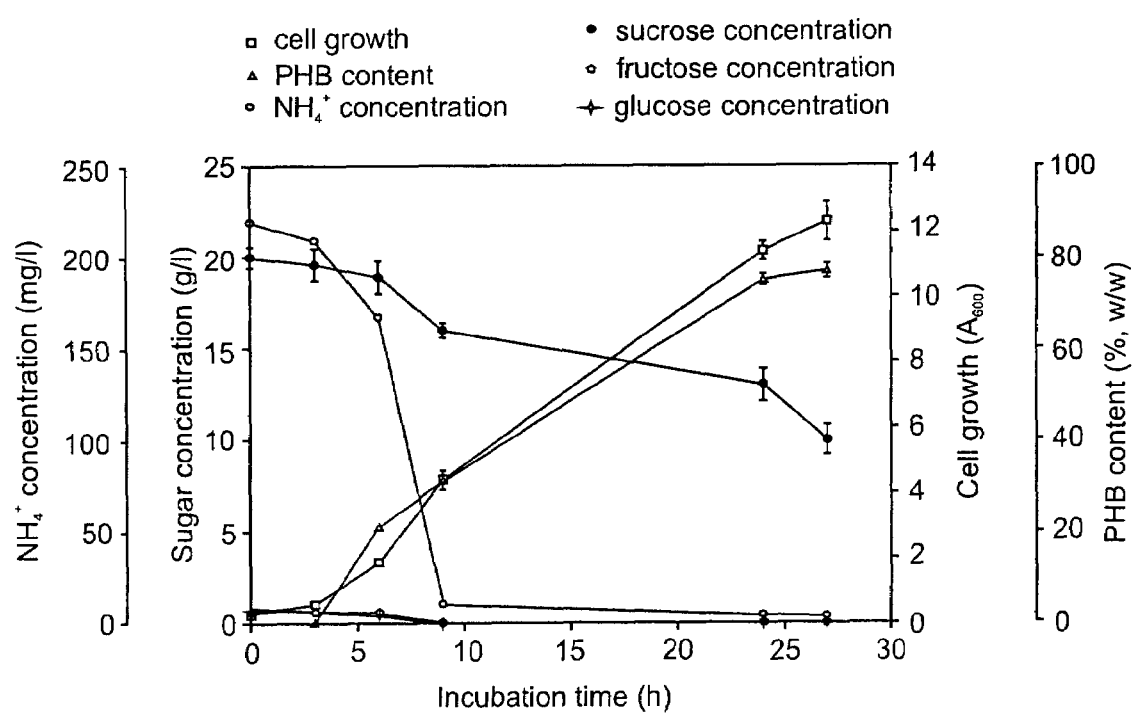
FIG. 2 depicts a graph of cell growth ($A_{600}$), sugar concentration (g/l), PHB content (% w/w) and $NH_4^+$ concentration (mg/l) versus incubation time (h) for a batch culture of *Alcaligenes latus* grown in a 10 L working volume fermenter using maple sap as sole carbon source; and, FIG. 3 depicts thermogravimetric analyses of purified PHB samples produced from (a) sucrose and (b) maple sap.

Reproducible results are vital to a systematic analysis of the influence of process development parameters on fermentation performance on a large scale. To ensure reproducibility of results obtained with shake flasks, batch fermentation in bench scale bioreactor (10 L working volume) was performed using maple sap as the sole carbon source for PHB production by *Alcaligenes latus*. FIG. 2 summarizes the growth of *A. latus* on maple sap based medium and the accumulation of PHB within the cells in a 10 L working volume fermenter. Residual glucose and fructose were consumed during the first 9 h of growth. PHB production was initially noticed after 6 h of incubation, a period marked by a sharp decrease in ammonium concentration. The depletion of ammonium coincided with the bacteria entering into a stationary growth phase and an accelerated consumption of sucrose. The PHB content increased but at a reduced rate after nitrogen exhaustion, reaching a maximum yield of 77 wt % after 27 h of incubation. PHB accumulation was found to be associated with cell growth and the consumption of sucrose.

The biomass and PHB content obtained with maple sap were comparable to those in shake flasks. The batch fermentation results confirmed the optimal conditions derived from the shake flask optimization studies (see Table 2). Thus maple sap could be used as a starting material for PHB production by *A. latus*.

TABLE 2

Comparison of PHB Production Between Shake Flasks and Fermenter[a]

| | Scale | | |
|---|---|---|---|
| | Shake Flask (100 ml) | | Fermenter (10 l) |
| | Sucrose | Maple Sap | Maple Sap |
| Dry Weight (g/l) | 2.9 ± 0.3 | 4.4 ± 0.5 | 4.23 ± 0.25 |
| PHB Content (wt %)[b] | 74.1 ± 2.0 | 77.6 ± 1.5 | 77.0 ± 2.6 |
| PHB Conc. (g/l)[c] | 2.15 | 3.41 | 3.26 |
| PHB Yield (g/g)[d] | 0.23 | 0.34 | 0.32 |

[a]Initial sucrose concentration was 20 g/l with an incubation time of 27 h. Each value is an average of three determinations.
[b]Percentage of PHB to cell dry weight.
[c]g PHB per liter of culture.
[d]g PHB per g of sucrose consumed.

Molecular weight of polymers is believed to be the most important factor affecting physical and mechanical properties, and thus dictate the range of applications in products. The weight average molecular weights (Mw) of PHB produced by *A. latus* from maple sap and pure sucrose media were 487,000±50,000 Da and 420,000±30,000 Da, respectively (see Table 3). These molecular weight data correspond well to those reported by Doi, 1990 obtained with *Alcaligenes eutrophus* fermentation in glucose. In sucrose based media Yamane et al., 1996 produced PHB with Mw of 316,000 Da in a high-cell-density fed-batch. culture of *A. latus*.

The relatively high molecular weight of the PHB produced by *A. latus* from maple sap suggests that the biopolymer has a degree of polymerization suitable for commercial utilization. Cox, 1994 reported that the mechanical properties of PHB decrease significantly below a Mw of 400,000 and the material is quite brittle below 200,000.

Table 3 shows that the polydispersity index (weight average molecular weight (Mw)/number average molecular weight (Mn)) of PHB obtained from maple sap-grown cells was slightly higher than values for sucrose-produced PHB. Polydispersity values (Mw/Mn) were lower than 2 under all conditions tested, indicative of the uniform PHB polymer chain formation within the cell cytoplasm.

The melting temperature (Tm) and enthalpy of fusion (ΔH) are also presented in Table 3. For PHB sample produced from sucrose, the melting temperature and enthalpy of fusion were 160-176° C. and 80-82.0 J/g. For PHB sample produced from maple sap, the melting temperature and enthalpy of fusion were 163-173° C. and 76-78.5 J/g. Melting temperature and enthalpy of fusion are in a typical range for pure 3-PHB homopolymer as reported by Lee at al., 2002 with melting temperature of 177° C. and enthalpy of fusion of 80 J/g. The high enthalpy of fusion suggests high crystalline nature of the recovered PHB which was calculated to be 55-56% and 52-53% in sucrose and maple sap, respectively.

Figure 3:
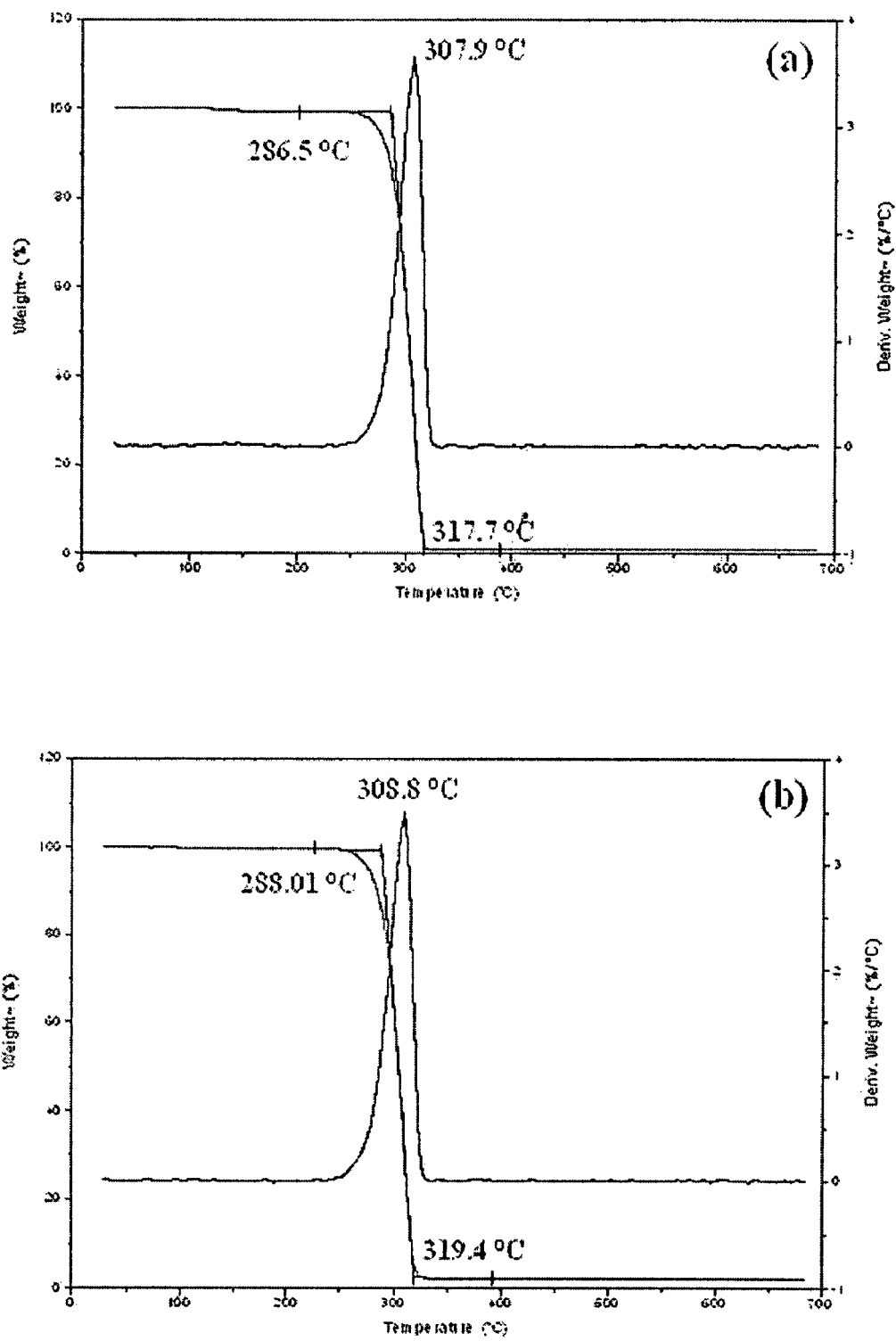

Thermogravemetric analyses of purified PHB samples produced by *A. latus* in sucrose and maple sap are illustrated in FIG. 3. In sucrose-based media, the recovered PHB showed a rapid thermal degradation between 286.5° C. and 317.7° C. with a peak at 307.9° C. In maple sap based media, the recovered PHB showed a rapid degradation between 288.01° C. and 319.4° C. with a peak at 308.8° C. The difference between the decomposition of the polymer and melting temperature of PHB samples produced in maple sap was high enough to facilitate processing of the biopolymer.

TABLE 3

Molecular Weight and Thermal Analysis of Purified PHB Samples

| | Sucrose | Maple Sap |
|---|---|---|
| Mw (Da) | 349, 849-490, 905 | 448, 606-525, 449 |
| Mn (Da) | 208, 571-418, 086 | 231, 994-363, 747 |
| Mw/Mn | 1.17-1.67 | 1.45-1.93 |
| Tm (° C.) | 160-176 | 163-173 |
| ΔH (J/g) | 80-82 | 76-78.5 |
| Crystallinity (%) | 55-56 | 52-53 |

REFERENCES

Agriculture and Agri-Food Canada, 2005. Canadian Maple Products: Situation and Trends (2004-2005). www.agr.gc.ca/misb/hort/sit/pdf/maplerable0506_e.pdf Barham P G, Keller A, Otum E L, Holmes A. 1984. Crystallization and morphology of a bacterial thermoplastic: poly-β-hydroxybutyrate. *J Mater Sci* 19:2781-2794.

Braunegg G, Bona R, Koller M. 2004. Sustainable polymer production. *Polymer-Plastics Technology and Engineering* 43:1779-1793.

Byrom D, 1990. Industrial production of Copolymer from *Alcaligenes eutrophus*. In: Dawes E A, editor. *Novel Biodegradable Microbial Polymers*. Amsterdam: Kluwer Academic. p 113-117.

Comeau Y, Hall K J, Oldham W K. 1988. Determination of poly-β-hydroxybutyrate and poly--hydroxyvalerate in activated sludge by gas-liquid chromatography. *Appl Environ Microbiol* 54:2325-2327.

Cox M K. 1994. Properties and applications of polyhydroxyalkanoates. In: Doi Y and Fukuda K editors. *Biodegradable plastics and polymers*. Amsterdam: Elsevier Science. p 120-135.

Doi Y. 1990. *Microbial polyesters*. New York: VHC Publishers Inc. 156 p.

Frazzetto G, 2003. White biotechnology. *EMBO Reports* 4:835-837.

Gavrilescu M, Chisti Y. 2005. Biotechnology: a sustainable alternative for chemical industry. *Biotechnol Adv* 23:471-499.

Gerngross T U. 1999. Can biotechnology move us toward a sustainable society? *Nature Biotechnology* 17:541-544.

Gerngross T U, Slater S C. 2000. How green are green plastics? *Scientific American* 283:37-41.

Gross R A, Kalra B. 2002. Biodegradable Polymers for the Environment. *Science* 297:803-807.

Grothe E, Moo-Young M, Chisti Y. 1999. Fermentation optimization for the production of poly(β-hydroxybutyric acid) microbial thermoplastic. *Enzyme Microbial Technol* 25:132-141.

Huyler N K. 2000. Cost of maple sap production for various size tubing operations. U.S. Dept. of Agriculture, Forest Service, Newtown Square, Pa.

Lee S N, Lee M Y, Park W H. 2002. Thermal stabilization of poly(3-hydroxybutyrate) by poly(glycidyl methacrylate). *J Appl Polymer Sci* 83:2945-2952.

Morin A, Heckert M, Poitras E, Leblanc D, Brion F, Moresoli C. 1995. Exopolysaccharide production on low-grade maple sap by *Enterobacter agglomerans* grown in small scale bioreactors. *J Appl Bacteriol* 79:30-37.

Morselli M F, Whalen M L. 1996. Maple chemistry and quality. In: Koelling M R and Heiligmann R B editors.

North American maple syrup producers manual. Columbus: The Ohio State University. p 162-171.

Palleroni N J, Palleroni A V. 1978. *Alcaligenes latus*, a new species of hydrogen-utilizing bacteria. *Int J Sys Bacteriol* 28:416-424.

Pradella J G. 2006. Biopolimeros e Intermediarios Quimicos. Centro de Tecnologia de Processos e Produtos, Relatorio Tecnico #84396-205, Sao Paulo, Brazil.

Rehm BHA, 2003. Polyester synthases: Natural catalysts for plastics. *Biochem J* 376:15-33.

Steinbuchel A, Hustede E, Liebergesell M, Pieper U, Timm A, Valentin H. 1992. Molecular basis for biosynthesis and accumulation of polyhydroxyalkanoic acids in bacteria. *FEMS Microbiol Rev* 103:217-230.

Wang F, Lee S Y. 1997. Poly(3-hydroxybutyrate) production with high productivity and high polymer content by a fed-batch culture of *Alcaligenes latus* under nitrogen limitation. *Appl Environ Microbiol* 63:3703-3706.

Whitney G G, Upmeyer M M. 2004. Sweet trees, sour circumstances: The long search for sustainability in the North American maple products industry. *Forest Ecology and Management* 200:313-333.

Woodward J, Orr M. 1998. Enzymatic conversion of sucrose to hydrogen. *Biotechnol Progr* 14:897-902.

Yamane T, Fukunaga M, Lee Y W. 1996. Increased PHB productivity by high-cell-density fed-batch culture of *Alcaligenes latus*, a growth-associated PHB producer. *Biotechnol Bioeng* 50:197-202.

Yezza A, Fournier D, Halasz A, Hawari J. 2006. Production of Polyhydroxyalkanoates from Methanol by a New Methylotrophic Bacterium *Methylobacterium* sp. GW2. *Appl Microbiol Biotechnol* 73:211-218.

Lambert et al., Canadian Patent Application 2,460,109, published Mar. 21, 2002.

Bright et al., U.S. Pat. 5,502,273, issued Mar. 26, 1996.

Martin et al., U.S. Pat. 6,083,729 issued Jul. 4, 2000.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. Process for producing poly-β-hydroxybutyrate comprising contacting unrefined maple sap with bacteria that convert sugars into poly-β-hydroxybutyrate, wherein the poly-β-hydroxybutyrate has a weight average molecular weight from about 487,000+/−50,000 Daltons and wherein the average molecular weight is determined by gel permeation chromatography.

2. Process according to claim 1, wherein the poly-β-hydroxybutyrate has a weight average molecular weight of 450,000 Daltons or greater.

3. Process according to claim 1, wherein the poly-β-hydroxybutyrate has a weight average molecular weight of 475,000 Daltons or greater.

4. Process according to claim 1, wherein the poly-β-hydroxybutyrate has a weight average molecular weight of 480,000 Daltons or greater.

5. Process according to claim 1, wherein the bacteria comprise one or more species of *Alcaligenes*.

6. Process according to claim 1, wherein the bacteria comprise *Alcaligenes latus*.

7. Process according to claim 1, wherein the bacteria comprise *Alcaligenes latus* and the poly-β-hydroxybutyrate has a weight average molecular weight of 450,000 Daltons or greater.

8. Process according to claim 1, wherein the bacteria comprise *Alcaligenes latus* and the poly-β-hydroxybutyrate has a weight average molecular weight of 475,000 Daltons or greater.

9. Process according to claim 1, wherein the bacteria comprise *Alcaligenes latus* and the poly-β-hydroxybutyrate has a weight average molecular weight of 480,000 Daltons or greater.

10. The process according to claim 1, wherein the bacteria are cultivated on the maple sap.

11. The process according to claim 6, wherein the bacteria are cultivated on the maple sap.

* * * * *